United States Patent
Valencia Avila et al.

(10) Patent No.: US 8,617,472 B2
(45) Date of Patent: Dec. 31, 2013

(54) SYSTEM FOR PROTECTING CIRCUITRY IN HIGH-TEMPERATURE ENVIRONMENTS

(75) Inventors: Benito Valencia Avila, Saillon (CH); Alec Ginggen, Neuchatel (CH)

(73) Assignee: Codman Neuro Sciences SARL (CH)

( * ) Notice: Subject to any disclaimer, the term of this patent is extended or adjusted under 35 U.S.C. 154(b) by 964 days.

(21) Appl. No.: 12/731,341

(22) Filed: Mar. 25, 2010

(65) Prior Publication Data

US 2010/0179477 A1    Jul. 15, 2010

Related U.S. Application Data

(63) Continuation of application No. 11/262,698, filed on Oct. 31, 2005, now Pat. No. 7,713,471.

(51) Int. Cl.
*G01D 11/26* (2006.01)
*H02H 5/04* (2006.01)
*H05B 6/04* (2006.01)
*A61B 1/00* (2006.01)

(52) U.S. Cl.
USPC ........... 422/109; 422/105; 422/108; 422/119; 361/103; 361/105; 361/93.8; 219/661; 219/668; 600/133; 600/151

(58) Field of Classification Search
USPC ........... 422/1–3, 26, 105, 108–109, 117, 119; 361/103, 105, 93.8, 125; 340/532, 593, 340/584; 219/69.19, 661, 668; 600/133, 600/549, 151; 73/649
See application file for complete search history.

(56) References Cited

U.S. PATENT DOCUMENTS

| | | | | |
|---|---|---|---|---|
| 4,329,568 A | * | 5/1982 | Rocher et al. | 219/497 |
| 4,901,060 A | * | 2/1990 | Liu | 340/598 |
| 5,081,988 A | * | 1/1992 | Cook et al. | 607/21 |
| 5,520,892 A | * | 5/1996 | Bowen | 422/295 |
| 6,072,680 A | * | 6/2000 | Goodwin et al. | 361/104 |
| 2003/0231990 A1 | * | 12/2003 | Faries et al. | 422/119 |

FOREIGN PATENT DOCUMENTS

| | | |
|---|---|---|
| EP | 676209 A1 | 10/1995 |
| JP | 1100994 A | 4/1989 |

* cited by examiner

*Primary Examiner* — Monzer Chorbaji

(57) ABSTRACT

An electrical device for performing a particular function includes a system circuit for performing the function, and a dedicated power supply for providing power to the circuit. Both the system circuit and the power supply are hermetically sealed within a housing. The device within the housing is intended to be sterilized using high temperature, reaching a sterilization temperature. According to the invention, the device includes a thermal switch which is electrically connected between the system circuit and the power supply. The thermal switch is switchable between an open position wherein the system circuit is electrically isolated from the power supply and receives no power therefrom and a closed position wherein the system circuit is electrically connected to the power supply and receives power therefrom. The thermal switch switches from its closed position to its open position in response to the temperature within the housing rising to a predetermined switch-open temperature value. The thermal switch thereafter switches from its open position to its closed position in response to the temperature within the housing cooling to a switch-closed temperature value. With the present invention, the electrical components of a device are automatically protected from thermal damage during sterilization.

2 Claims, 3 Drawing Sheets

SYSTEM FOR PROTECTING CIRCUITRY IN HIGH-TEMPERATURE ENVIRONMENTS

CROSS REFERENCE TO RELATED APPLICATION

Figure 1:
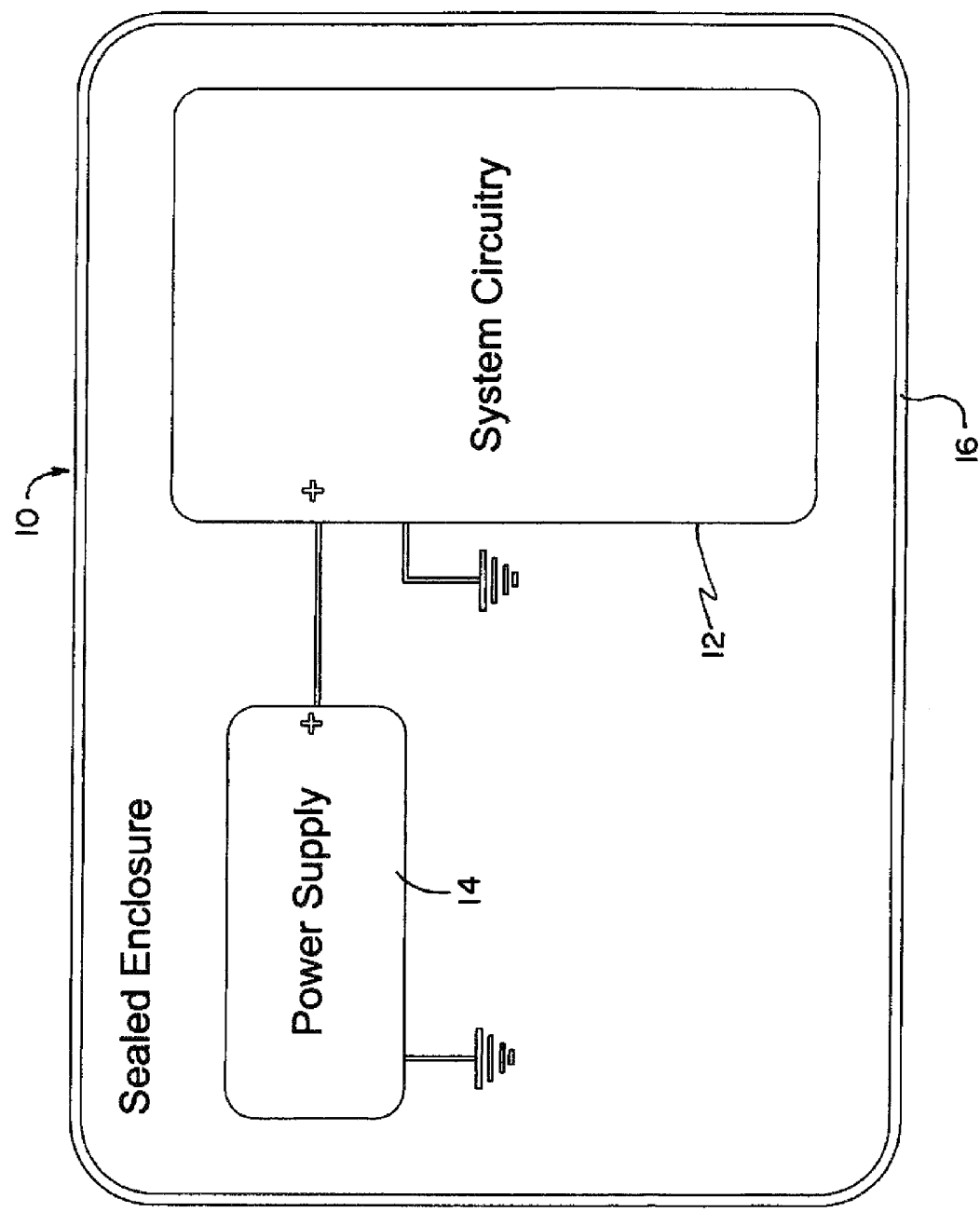

The present application is a continuation of pending U.S. application Ser. No. 11/262,698, filed Oct. 31, 2005.

BACKGROUND OF THE INVENTION

1) Field of the Invention

This invention generally relates to high-temperature sterilization of electronic devices and electromechanical devices and, more particularly, to systems to protect electronic components against the damaging effects of high-temperature sterilization.

2) Discussion of Related Art

Excess thermal energy (i.e., heat) is generally considered undesirable and harmful to electronic circuits. Electronic components of consumer and military electronic devices are each designed to operate within a specific temperature range, depending on the anticipated operational environment and the expected service parameters of the particular component. Generally, the higher the temperature that a particular electronic device or component can withstand without operational failure (or shortened lifespan), the more expensive that component will be to manufacture. Any device which requires many of such high-temperature-rated components, will, of course, end up being expensive as well.

Essentially, all electronic components generate some heat by dissipating energy as they operate. To this end, effective thermal management is important so that the upper end of the operational temperature range may be increased without the component failing. Most semiconductor devices, for example, are not rated for junction temperatures above 175° C., and their performance degrades rapidly with increased temperatures exceeding that upper limit, especially if the applied high temperature is maintained for relatively long periods of time. Interestingly, electronic components that are operating under power are substantially more sensitive to thermal damage than the same components isolated from a power source.

It is common to design thermal management structures and systems into a circuit to help prevent thermal-related failure of the operating components. Most thermal management includes mechanical heat-conduction structure designed to draw heat energy away from the electronic devices, as the heat is generated within or adjacent the component. Such structure includes heat sinks, cooling fans, and liquid-cooling systems, etc.

These cooling systems generally work well at removing excess heat from an operating electronic device because in most cases, there is access to a cooler region into which the excess energy generated by the particular electronic component may easily and naturally migrate, resulting in a cooler operating component. Unfortunately, certain electronic devices are forced to operate in a super-heated environment for a prolonged period of time (between 2 and 120 minutes depending on the sterilization temperature, device size, mass and complexity) where, by the very nature of the environment, no such temperature gradient can effectively exist.

A variety of mechanical and electro-mechanical devices must operate in environments that require the devices to be completely isolated within a protective barrier. In some situations, the "outside environment" (environment located outside the barrier) is hazardous and includes elements or conditions that will adversely affect the operation of the device or shorten its expected useful operative life. In such hazardous environments, the device must be completely sealed and the protective barrier must be made with the particular hazard in mind. For example, implanted devices must be hermetically sealed to prevent the penetration of moisture, which would adversely affect the operation of the device. Also, many medical devices that are to be implanted within a human patient, for example, must also be hermetically sealed, primarily, in this delicate living environment, to prevent infection or contamination caused from within the device.

Certain biologically implanted devices include delicate electronic components typically including integrated circuits, memory chips, and solid state sensors, that are powered by on-board, hermetically-sealed batteries and are all sensitive to high temperatures. Pace-makers, defibrillators, stimulators, drug-delivery devices (such as infusion pumps) are some examples of such powered, implanted devices wherein, for biological-safety reasons, the electronic components and the power supply are both permanently sealed within a metal housing and owing to the sealed arrangement requirements, cannot be mechanically or electrically accessed from outside the housing. The batteries used are built into the device and will provide the necessary power for the operational life of the device.

After manufacture of such devices and prior to them being used (or surgically implanted within a patient), the entire device must be sterilized using either a gas-sterilization system, a gamma radiation system or steam. If a gas is used, typically, Ethylene Oxide (ETO) is applied to the device for a controlled period of time. Sterilizing using ETO may be effective, but many materials tend to absorb the ETO chemical during the process. These components must be properly aerated after the ETO gas has been applied. Furthermore, in such applications wherein the sterilized device contacts humans, new studies have shown that an increasing number of people are sensitive to even the trace amounts of ETO residing on the device after ETO sterilization is complete.

Gamma radiation or E-beam application may be applied to the device to effectively sterilize the entire device, but unfortunately, such radiation applications have been shown to degrade or otherwise damage certain plastic and rubber compounds and, sadly, also electronic components.

Steam sterilization is a simple and effective process and is generally preferred over using ETO or gamma radiation. However, since the system uses heat to kill any microbes on the device, the required temperatures can likely damage onboard electronic components and onboard batteries.

To ensure thorough sterilization, super-heated steam is applied to the hermetically-sealed electronic device for a period generally between 2 and 120 minutes (depending on the sterilization temperature, device size, mass and complexity), during which time the entire device, including any onboard circuitry and batteries will become super-heated. During the sterilization process, all of the components of the device will eventually reach a temperature between 120 and 135 degrees Celsius. Electronic circuits operating in this super-heated environment (while electrically connected to the on-board batteries) for such a prolonged period of time will invariably suffer irreparable thermal damage and will likely fail either immediately, or sometime before its expected operational life has been reached. This potential for failure is incredibly undesirable considering that the device will eventually operate long-term within a human and will likely help the human to live.

Of course, some of the heat-related damage caused by the steam-sterilization process can be mitigated by using highspecification components (e.g., military-spec components). These components undergo critical testing during their manufacture and have been otherwise designed to handle higher temperatures. The problems associated with these military grade components include size, availability, and cost. The military grade components are generally larger and more expensive than their equivalent commercial-grade components. Furthermore, not all components are available in military grade. Considering typical commercial viability of the end product and the limited space available, use of such expensive and larger military-spec components is generally difficult to justify, leaving little option but to rely on cheaper, smaller, yet more-heat sensitive components for many of the devices that must be sterilized.

It is therefore an object of the present invention to provide a thermal-related protection to electronic components, which overcomes the deficiencies of the prior art.

SUMMARY OF THE INVENTION

An electrical device for performing a particular function includes a system circuit for performing the function, and a dedicated power supply for providing power to the circuit. Both the system circuit and the power supply are hermetically sealed within a housing. The device within the housing is intended to be sterilized using high temperature, reaching a sterilization temperature. According to the invention, the device includes a thermal switch, which is electrically connected between the system circuit and the power supply. The thermal switch is switchable between an open position wherein the system circuit is electrically isolated from the power supply and receives no power therefrom and a closed position wherein the system circuit is electrically connected to the power supply and receives power therefrom. The thermal switch switches from its closed position to its open position in response to the temperature within the housing rising to a predetermined switch-open temperature value. The thermal switch thereafter switches from its open position to its closed position in response to the temperature within the housing cooling to a switch-closed temperature value. With the present invention, the electrical components of a device are automatically protected from thermal damage during sterilization.

BRIEF DESCRIPTION OF THE DRAWING FIGURES

Figure 2:
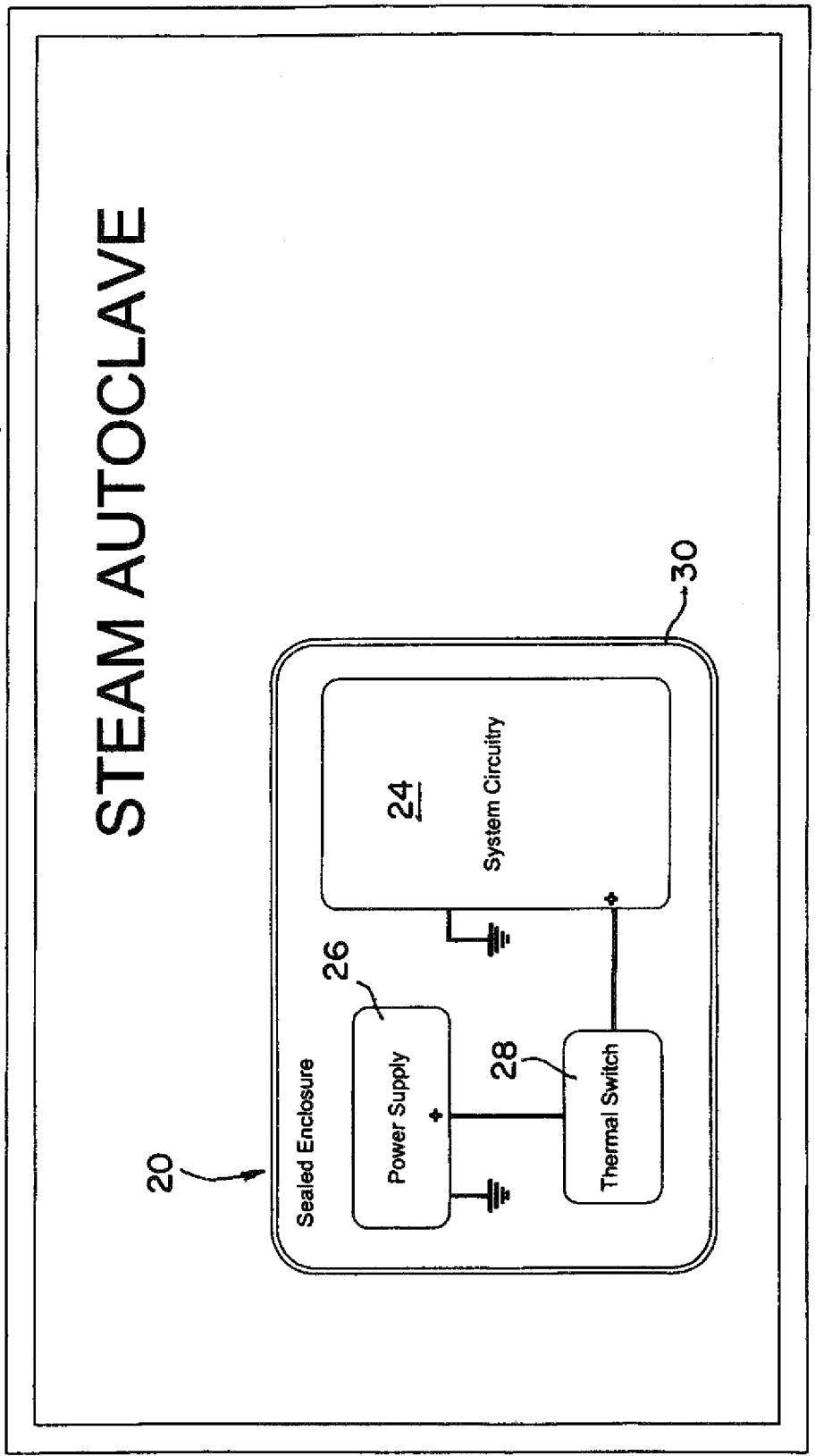
Figure 3:
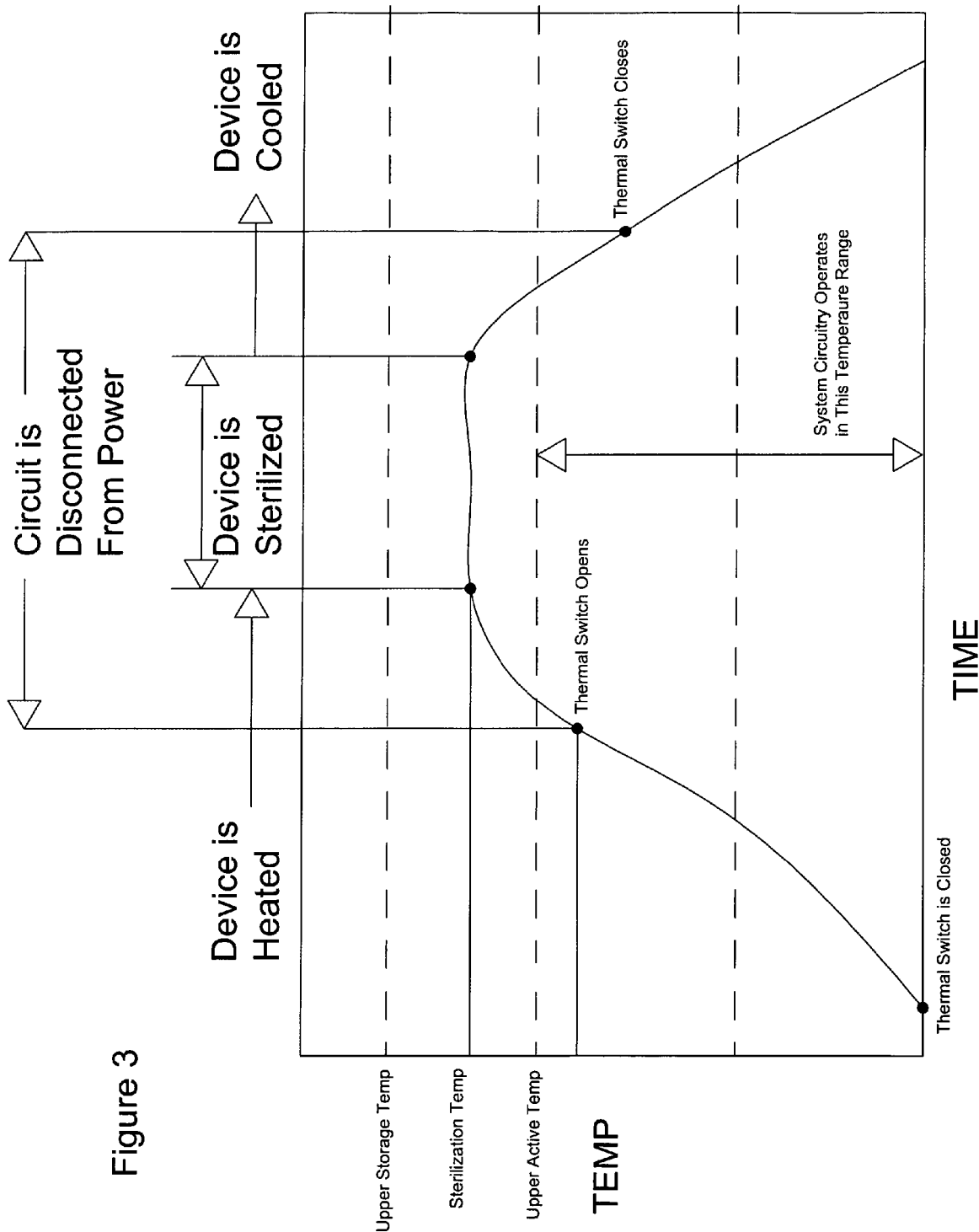

FIG. 1 (labeled "prior art") is a sectional plan view of an exemplary sterilizable electrical device including a housing containing a hermetically sealed systems circuit and a hermetically sealed battery, according to the prior art;

FIG. 2 is a sectional plan view of an exemplary sterilizable device including a housing containing a hermetically-sealed systems circuit, a hermetically-sealed battery and a hermetically-sealed thermal switch, wherein the device is shown inside an steam autoclave, according to the present invention; and FIG. 3 is a graph representing sterilization temperature of the device during a period of time, wherein the thermal switch within the device becomes electrically open at a predetermined rising temperature and re-closes at a predetermined cooling temperature, according to the present invention.

DETAILED DESCRIPTION OF THE PRESENT INVENTION

Further details, features and advantages of the invention are shown in the following description of an exemplary embodiment by reference to the drawings.

Referring to FIG. 1, labeled "prior art", an exemplary electrical device 10 is shown including system circuitry 12, a power supply 14 and a housing 16. System circuitry 12 includes a least one electrically powered component (not shown) and is powered by power supply 14. Power supply 14 is typically a long-life battery and is designed to supply sufficient power to the system circuitry 14 so that the electrical device may operate the entirety of its predetermined useful life. In a variety of situations, both the power supply 14 and the system circuitry 12 of device 10 are hermetically sealed within the housing 16. Housing 16 is made from an appropriate material, depending on the intended environment, usually metal or plastic.

As discussed in the Background of the Invention section above, certain types of these hermetically-sealed electrical devices 10 must be sterilized throughout the entire housing. It is preferred to perform the sterilization process after the device is fully manufactured and already sealed in its housing. One of the most efficient and thorough sterilization processes in such instance includes subjecting the entire device 10 to a high-temperature steam environment, such as the environment produced by an autoclave. The steam provides an effective medium for transferring thermal energy into the housing 16. After a predetermined period of time, sufficient energy from the steam transfers (through both conduction and convention) to within the housing 16 so that every point within the device would have increased in temperature to a point that all possible microbes located anywhere within the device would die. A typical sterilization time, for example for an infusion pump is between 2 and 120 minutes depending on the sterilization temperature, the device size, mass and complexity, at a temperature between 120 and 135 degrees Celsius.

Unfortunately, since the electrical components of the system circuitry 12, and the power supply 14 of the exemplary prior art device 10 shown in FIG. 1 are hermetically sealed within housing 16, they are not readily or easily accessible. Therefore, the electrical components within the sealed housing cannot be disconnected from the power supply, for example during a sterilization procedure, and therefore must remain powered during any sterilization process. If high-temperature thermal transfer is used during the sterilization process, the powered onboard electrical components of the device 10 will likely become damaged and will fail either during the sterilization process, or shortly thereafter.

As described above, in the Background of the Invention section, high grade, so-called military-grade electrical components may be used in the design of the electrical device 10 to help survive the high-temperatures of sterilization. Such military components are designed to handle much higher temperatures, even when continuously powered by a power supply. However, as described above, use of such high-performance electrical components is somewhat discouraged wherever possible in the design process of many electrical devices owing to the much higher cost to implement the military grade components. Typically, the up to 120 minutes or so minutes that the device is being sterilized is the only time the device will experience such high-temperatures so it is difficult to justify the larger, more expensive military components for the device 10.

According to the present invention and referring to FIG. 2, an electrical device 20 is shown positioned within a steam autoclave 22. The device includes system circuitry 24, a power supply 26, and a temperature-responsive electrical switch 28 (a thermal switch), which are all enclosed in a hermetically sealed housing 30. According to the invention, the temperature-responsive switch 28 is used to automatically disconnect the system circuitry 24 from the power supply 26 in response to the interior temperature of the housing 30 reaching a predetermined temperature. By electrically disconnecting the system circuitry 24 from the source of power, the electrical components that make up the circuit of the device will be able to withstand a much higher temperature without becoming damaged, in particular, the high-temperature that the device 20 will reach when subjected to a steam-sterilization environment.

Referring now to FIG. 3, a Temperature by Time graph is shown to illustrate how the temperature inside the housing 30 containing the temperature-sensitive switch of the present invention varies during a steam sterilization process. The graph is intended to show relative variations throughout the sterilization process as well as help explain the operation of the cutoff switching system located within device 20 and shown in FIG. 2. To this end, the graph includes no numerical data.

To begin sterilization, at least one device 20 is positioned within a sterilization chamber, such as the steam autoclave 22 shown in FIG. 2. At this point, the device 20 is operational in that the thermal switch 28 is electrically closed and the hermetically sealed system circuitry 24 is electrically connected to power supply 26 and all the onboard electrical components are considered active (powered). When active, the electrical components will typically operate within an operational temperature range. The components will also include an active temperature range that has an upper active temperature limit, above which the components will likely fail, or otherwise become damaged by the increasing thermal energy reaching the components. The graph of FIG. 3 shows the "Upper Active Temp" along the vertical TEMP axis to illustrate this upper limit, as well as the range of temperature that an electronic component will normally operate.

As introduced above, all electronic components generate some heat by dissipating energy as they operate. Additional heat energy may enter the components by convention and conduct from the surrounding environment. Each electronic component will operate (under power) within a prescribed operational temperature range. Should the total heat energy collected within the electronic device rise above the upper limit of the prescribed operational temperature range, the electronic device is likely to fail and become permanently damaged. Most semiconductor devices, for example, are not rated for junction temperatures above 175° C., and their performance degrades rapidly with increased temperatures exceeding that upper limit, especially if the applied high temperature is maintained for relatively long periods of time, such as the temperatures that are reached during a steam-sterilization process. Should electronic devices remain operational (i.e., connected to power) during the steam-sterilization process, the device will likely become permanently damaged due to the collected thermal energy.

As further mentioned above, electronic components operating under power are substantially more sensitive to thermal damage than the same components isolated from a power source. Once disconnected from a power source, the electronic device can withstand absorbing greater thermal energy, defining an upper storage temperature, above which, the electronic device will likely become damaged, regardless of the power. As defined, the storage temperature range, including an upper storage temperature, is the range of temperature within which an electrically-isolated (i.e., power off) electronic component can survive without damage. As further defined, the operational (or active) temperature range, including an upper active temperature, is the range of temperature within which an electrically-connected (i.e., powered) electronic component can survive without damage. By this definition, according to the present invention, the upper storage temperature is higher in magnitude than the upper active temperature.

According to the invention, the thermal switch is electrically closed prior to the chamber 22 being heated, as shown at the start of the plotted curve in the graph of FIG. 3.

Once in position, the chamber 22 is sealed and heat is applied and transferred throughout the chamber by steam. The sterilization process includes a heating period, during which the device is heated, a sterilization period, during which the temperature within the chamber has reached a predetermined sterilization temperature, and a cooling period.

As the heating period begins, the steam immediately begins to transfer heat energy to the enclosed housing 30 of the device 20 and soon after, the temperature within the hermetically sealed housing 30 begins to rise, as shown by the single plotted line of the graph of FIG. 3. Eventually, the temperature within the device 20 reaches a point where the thermal switch 28 is responsive to electrically open. This action will cause the onboard system circuitry 24 to electrically disconnect from the onboard power supply 26. When the circuitry components are no longer powered (or active), they will assume a storage temperature range, which has an upper limit, above which, the inactive components will become damaged by elevated temperature. This "upper storage temp", which is shown in the graph along the TEMP axis will have a value that is greater than the upper active temperature and must be also be greater than the highest temperature reached during the entire sterilization temperature (which is also shown in the graph). As long as the sterilization temperature remains lower than the upper storage temperature, the electrical components will be safe from thermal damage caused by the sterilization process.

Eventually, the device and all of the onboard components will reach a sterilization temperature, as illustrated by the relatively flat upper portion of the plotted curve. This temperature must be maintained for a period of time. A period of time that would have been previously determined by experimentation to be sufficient to kill a predetermined percentage of a known bacteria. Once this percentage of bacteria is killed by the elevated temperatures during sterilization, the device would be considered "sterilized". After the period of time has passed, the cooling period may begin, according to the invention.

Once the device is considered sterilized, the temperature within the chamber 22 is reduced. At a certain predetermined temperature, the thermal switch will respond and actively electrically close. This action will electrically reconnect the onboard system circuitry 24 with the power supply 26. The temperature at which the thermal switch closes will likely be less than the temperature at which the thermal switch opened (during the heating period), depending on the particular specifications of the switch.

The graph clearly illustrates that the upper storage temperature of the onboard inactive components remains greater than the highest sterilization temperature reached during the sterilization process. This ensures that the onboard components will remain undamaged during sterilization.

After the cooling period is complete and the thermal switch closes, the device 20 will again be powered and operational when it is removed from the chamber 22.

According to a first preferred embodiment of the invention, the thermal switch 28 is a passive switching mechanism that operates using a bi-metallic actuator. As is understood by those skilled in the art, the bimetallic actuator is preformed at a cool temperature and will "snap" (or otherwise deform) to a different shape when a critical threshold temperature is reached. The deformed shape will remain until a lower "return" temperature is reached, at which point the original starting shape will return. The actuator is typically integrated with electrical contacts so that the contacts will open and close as the actuator changes its shape, in response to the temperature.

This type of thermal switch is preferred primarily because it is designed to operate in a predictable manner in a high temperature environment. It also does not use any power to operate, it is repeatably reliable, it is typically an "off the shelf" part and is available in a wide variety of temperature thresholds and hysteresises.

According to a second embodiment of the invention, thermal switch 28 is made using shaped memory alloy (SMA). Basically similar to bimetallic materials, SMAs are materials that hold a preset shape until a critical temperature is reached, after which the material automatically transforms to a second shape. This transition is relied upon to selectively connect an electrical circuit in response to the surrounding temperature. Again, the thermal switch of this second embodiment requires no power to operate, but is less available than the above-described bimetallic switch and typically must be custom made.

According to a third embodiment of the invention, thermal switch 28 is based on an active electrical circuit that is designed to switch off as the surrounding temperature reaches a predefined threshold temperature. One such circuit is based on a positive temperature coefficient resistor (a PTC resistor) whose resistance markedly increases when a predetermined temperature is reached. The sudden increase in resistance can be detected using a simple comparator circuit using an operational amplifier and a few resistors of known value. This type of circuit can utilize other temperature responsive components in place of the PTC resistor, as is well known to those of skill in the art.

Although this third embodiment would be accurate and reliable, the components that make up this thermal-sensitive circuit would require an upper active temperature limit that is above the sterilization temperature and would therefore likely be military grade and expensive. Also, this circuit would always draw power from the power supply regardless of the connection between the system circuit and the power supply.

Applicant understands that many other systems exist that may be used to electrically disconnect a system circuitry from a power supply. Although not mentioned in any detail here, it should be understood that any of these systems can be integrated within the present invention, in place of the thermal switch, without departing from the gist of the invention.

What is claimed is:

1. An electrical device for performing a particular function, said device being of the type that requires sterilization using heat, said sterilization process reaching a sterilization temperature, said device comprising:
   a system circuit for selectively performing said particular function;
   a power supply for selectively providing sufficient power to said system circuit to allow said system circuit to perform said particular function;
   a housing for containing said system circuit, said housing being hermetically sealed; and
   a thermal-switch electrically connected between said power supply and said system circuit, said thermal switch being switchable between an open position wherein said system circuit is electrically isolated from said power supply and receives no power therefrom and a closed position wherein said system circuit is electrically connected to said power supply and receives power therefrom, said thermal switch switching from said closed position to said open position in response to the temperature within said housing rising to a predetermined switch-open temperature value, said thermal switch thereafter switching from said open position to said closed position in response to the temperature within said housing cooling to a switch-closed temperature value, said system circuit when said thermal-switch being in said open position being protected from thermal damage during sterilization, wherein said thermal switch is positioned outside said housing.

2. An electrical device for performing a particular function, said device being of the type that requires sterilization using heat, said sterilization process reaching a sterilization temperature, said device comprising:
   a system circuit for selectively performing said particular function;
   a power supply for selectively providing sufficient power to said system circuit to allow said system circuit to perform said particular function;
   a housing for containing both said system circuit and said power supply, said housing being hermetically sealed; and
   a thermal-switch electrically connected between said power supply and said system circuit, said thermal switch being switchable between an open position wherein said system circuit is electrically isolated from said power supply and receives no power therefrom and a closed position wherein said system circuit is electrically connected to said power supply and receives power therefrom, said thermal switch switching from said closed position to said open position in response to the temperature within said housing rising to a predetermined switch-open temperature value, said thermal switch thereafter switching from said open position to said closed position in response to the temperature within said housing cooling to a switch-closed temperature value, said system circuit when said thermal-switch being in said open position being protected from thermal damage during sterilization, wherein said thermal switch is positioned outside said housing.

\* \* \* \* \*